United States Patent
Davis et al.

(10) Patent No.: US 9,310,351 B2
(45) Date of Patent: Apr. 12, 2016

(54) SYSTEMS AND METHODS OF DETECTING AND DEMONSTRATING HAIR DAMAGE VIA EVALUATION OF PROTEIN FRAGMENTS

(71) Applicant: The Procter & Gamble Company, Cincinnati, OH (US)

(72) Inventors: Michael Glenn Davis, Lebanon, OH (US); Michael Joseph Flagler, Cincinnati, OH (US); Yiping Sun, Mason, OH (US); Tanuja Chaudhary, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 10 days.

(21) Appl. No.: 14/217,977

(22) Filed: Mar. 18, 2014

(65) Prior Publication Data
US 2014/0197309 A1 Jul. 17, 2014

Related U.S. Application Data

(62) Division of application No. 13/109,546, filed on May 17, 2011, now abandoned.

(60) Provisional application No. 61/389,469, filed on Oct. 4, 2010, provisional application No. 61/345,321, filed on May 17, 2010, provisional application No. 61/354,397, filed on Jun. 14, 2010.

(51) Int. Cl.
*G01N 33/483* (2006.01)
*H01J 49/00* (2006.01)
*G01N 33/68* (2006.01)

(52) U.S. Cl.
CPC ........ *G01N 33/4833* (2013.01); *G01N 33/6839* (2013.01); *G01N 33/6851* (2013.01);
(Continued)

(58) Field of Classification Search
CPC .......... G01N 33/6839; G01N 33/6848; G01N 33/6824; C07K 1/128
See application file for complete search history.

(56) References Cited

U.S. PATENT DOCUMENTS 5,047,292 A  9/1991  Sadanobu et al.
5,068,315 A  11/1991  Buultjens et al.
(Continued)

FOREIGN PATENT DOCUMENTS

CN  1438242  8/2003
CN  101007847  8/2007
(Continued)

OTHER PUBLICATIONS

A simple and sensitive technique, based on protein loss measurements, to assess surface damage to human hair Sukhvinder S. Sandhu and Clarence R. Robbins J. Soc. Cosmet. Chem., 44, 163-175 (May/Jun. 1993).*
(Continued)

*Primary Examiner* — Krishnan S Menon
*Assistant Examiner* — Dwan A Gerido
(74) *Attorney, Agent, or Firm* — Angela K. Haughey

(57) ABSTRACT

Embodiments of a method for demonstrating type and/or source of hair damage comprises extracting protein fragments from a hair sample with an aqueous solution, testing the resulting protein fragments with the MALDI-MS test, and then either comparing the results between a damaged sample and an undamaged sample or comparing the results between a damaged sample and a list of known marker protein fragments to identify the type and/or source of the damage.

1 Claim, 1 Drawing Sheet

(52) U.S. Cl.
CPC ......... *H01J49/0036* (2013.01); *G01N 33/6824* (2013.01); *G01N 33/6848* (2013.01); *G01N 2333/4742* (2013.01)

(56) References Cited

U.S. PATENT DOCUMENTS

| | | | |
|---|---|---|---|
| 5,910,419 | A | 6/1999 | Johnson et al. |
| 6,902,721 | B1 | 6/2005 | Mundy et al. |
| 6,958,220 | B2 | 10/2005 | Mundy et al. |
| 7,253,341 | B2 | 8/2007 | Wang et al. |
| 7,955,810 | B2 | 6/2011 | Agus et al. |
| 8,252,753 | B2 | 8/2012 | Kurfurst et al. |
| 8,299,013 | B2 | 10/2012 | Van Dyke |
| 2002/0051760 | A1 | 5/2002 | Hirai et al. |
| 2004/0096815 | A1 | 5/2004 | Perrier et al. |
| 2005/0074763 | A1 | 4/2005 | Wang et al. |
| 2005/0152860 | A1 | 7/2005 | Yaar et al. |
| 2006/0088852 | A1 | 4/2006 | Petersohn et al. |
| 2006/0140893 | A1 | 6/2006 | Peron et al. |
| 2006/0172298 | A1 | 8/2006 | Wang et al. |
| 2007/0184511 | A1 | 8/2007 | Dawson et al. |
| 2007/0243098 | A1 | 10/2007 | Ohnishi et al. |
| 2007/0249000 | A1 | 10/2007 | Tuse et al. |
| 2007/0274936 | A1 | 11/2007 | Kurfurst et al. |
| 2008/0193962 | A1 | 8/2008 | Wada et al. |
| 2008/0274165 | A1 | 11/2008 | Van Dyke |
| 2008/0317730 | A1 | 12/2008 | Gennero et al. |
| 2009/0004242 | A1 | 1/2009 | Van Dyke |
| 2009/0053707 | A1 | 2/2009 | Yaar et al. |
| 2009/0137786 | A1 | 5/2009 | Yamauchi |
| 2009/0209738 | A1 | 8/2009 | Cranston et al. |
| 2009/0253125 | A9 | 10/2009 | Wang et al. |
| 2010/0055697 | A1 | 3/2010 | Agus et al. |
| 2010/0099200 | A1 | 4/2010 | Nazabal et al. |
| 2010/0233718 | A1 | 9/2010 | Aubert et al. |
| 2011/0281256 | A1 | 11/2011 | Davis et al. |
| 2011/0281366 | A1 | 11/2011 | Davis et al. |
| 2013/0174863 | A1 | 7/2013 | Marsh et al. |

FOREIGN PATENT DOCUMENTS

| | | |
|---|---|---|
| CN | 101054579 | 10/2007 |
| CN | 101457218 | 6/2009 |
| CN | 101458238 | 6/2009 |
| FR | 2911778 | 8/2008 |
| GB | 2352298 A | 1/2001 |
| JP | 02057182 | 2/1990 |
| JP | 8012530 | 1/1996 |
| JP | 09169800 | 8/1996 |
| JP | 11071398 | 3/1999 |
| JP | 2003113200 | 4/2003 |
| JP | 2004286738 | 10/2004 |
| JP | 2005002068 | 1/2005 |
| JP | 2005110602 | 4/2005 |
| JP | 2008056579 | 3/2008 |
| JP | 2008056614 | 3/2008 |
| JP | 2009057334 | 3/2009 |
| JP | 2009096774 | 5/2009 |
| JP | 2009107977 | 5/2009 |
| JP | 2010112788 | 5/2010 |
| KR | 010035745 | 5/2001 |
| WO | 84 00172 | 1/1984 |
| WO | 01 85964 | 11/2001 |
| WO | 0200016 A1 | 1/2002 |
| WO | 2005077319 A2 | 8/2005 |
| WO | 2006097205 | 9/2006 |
| WO | 2008028779 A1 | 3/2008 |
| WO | 2008055196 A2 | 5/2008 |
| WO | 2008074595 | 6/2008 |

OTHER PUBLICATIONS

MALDI MS in Analysis of Keratin Fibre Proteins Andrea Korner Springer Science + Business Media B. V. 2008.*
6th World Congress for Hair Research, Experimental Dermatology, vol. 19, No. 6, 33, May 20, 2010, pp. 566-566.
Taichi Habe et al.: "ToF-SIMS characterization of the lipid layer on the hair surface. I: the damage caused by chemical treatments and UV radiation", Surface and Interface Analysis, vol. 43, No. 1-2, May 11, 2010, pp. 410-412.
PCT International Search Report dated Nov. 2, 2011.
Investigating the Relationship Between the Hair Fibre Proteome and Hair Quality, Heywood et al., 22nd IFSCC International Congress, Cosmetic Science for a Global Marketplace, Sep. 23-26, 2002, Edinburgh, Scotland, United Kingdom.
Medicinal Sage, a Raw Material for Cosmetics with Good Prospects, Eritsyan, 6th International Scientific-Practical Conference "Cosmetic Products and Raw Materials: Efficacy and Safety", Moscow, Russia, Nov. 20-21, 2001, 146-147.
A Method to Determine Oxidised Proteins in Huam Stratum Corneum, Richert et al, Proceedings of the 19th IFSCC Congress, Sydney, Australia, Oct. 1996.
Species Identification of Oetzi's Clothing With Matrix-Assisted Laser Desorption/ionization Time-of-Flight Mass Spectrometry Based on Peptide Pattern Similarities of Hair Digests, Hollemeyer et al., Rapid Communications in Mass Spectrometry 2008; 22: 2751-2767.
A Smart Cyclopeptide Mimics the RGD Containing Cell Adhesion Proteins at the Right Site, Anzali et al., SOFW-Journal 135, Dec. 2009.
Labile Proteins Accumulated in Damaged Hair Upon Permanent Waving and Bleaching Treatments, J. Cosmet. Sci., 53, 337-344 (Nov./Dec. 2002).
Influence of Oxidative and/or Reductive Treatment on Human Hair (I): Analysis of Hair-Damage after Oxidative and/or Reductive Treatment, Journal of Oleo Science, vol. 52, No. 10, 541-548 (2003).
A Simple and Sensitive Method Using Protein Loss Measurements to Evaluate Damage to Human Hair During Combing, J. Soc. Cosmet. Chem., 46, 39-52 (Jan./Feb. 1995).
A Simple and Sensitive Technique, Based on Protein Loss Measurements, to Assess Surface Damage to Human Hair, J. Soc. Cosmet. Chem., 44, 163-175 (May/Jun. 1993).
PCT International Search Report dated Aug. 2, 2011.
Koufuchi Ryo, "Measurement of hair element by inductively coupled plasma mass spectrometer—Application to anti-aging medical science", Journal of Japanese Society for Dental Materials and Devices, May 25, 2010, vol. 29, No. 3, p. 246-248.
A Simple and Sensitive Technique, Based on Protein Loss Measurements, to Assess Surface Damage to Human Hair, Sukhvinder S. Sandho and Clarence R. Robbins, J. Soc. Cosmet. Chem., 44, 163-175 (May/Jun. 1993).
MALDI MS in Analysis of Keratin Fibre Proteins, Andrea Korner, Springer Science and Business Media B.V. 2008.

* cited by examiner

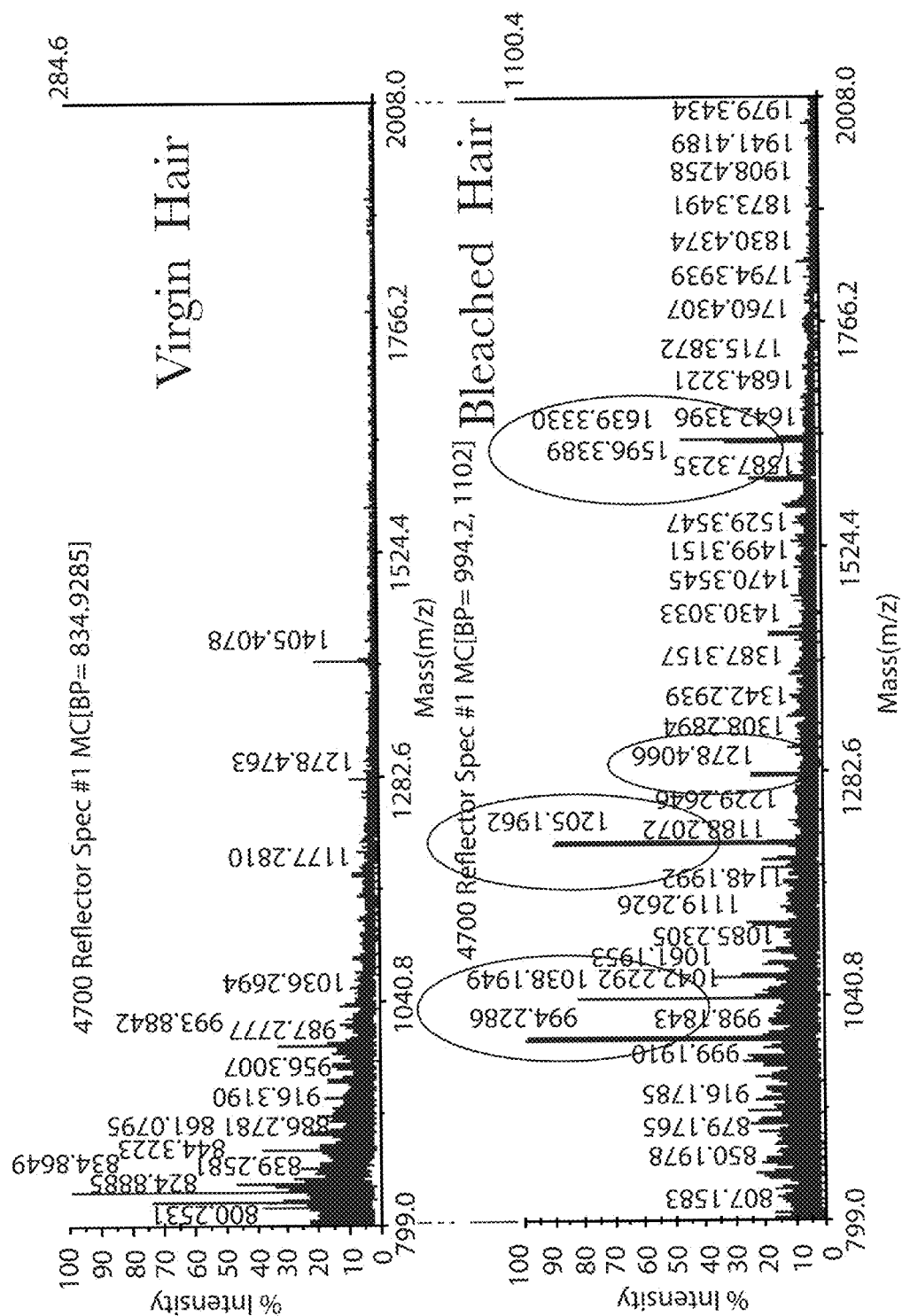

SYSTEMS AND METHODS OF DETECTING AND DEMONSTRATING HAIR DAMAGE VIA EVALUATION OF PROTEIN FRAGMENTS

CROSS REFERENCE TO RELATED APPLICATION

This application claims the benefit of U.S. Provisional Application No. 61/345,321 filed May 17, 2010 and U.S. Provisional Application No. 61/354,397 filed Jun. 14, 2010 and U.S. Provisional Application No. 61/389,469 filed Oct. 4, 2010.

FIELD OF THE INVENTION

Embodiments of the present disclosure are directed to a process for measuring the damage to the hair by the evaluation and identification of extracted protein fragments.

BACKGROUND OF THE INVENTION

Hair damage through protein loss is a known problem; however, most people have no recognition of the amount of protein loss experienced by their hair, or their level of hair health in general. Protein loss may be caused by everyday occurrences and environmental factors such as UV ray exposure, bleaching, coloring, perming, straightening, mechanical manipulation, and salt water contact.

Proper hair architecture at the molecular level is an important characteristic of hair that has a healthy look, shine and feel. The hair comprises mostly protein and is not regenerative after it exits the scalp. Therefore, it is valuable to have products which protect the overall protein integrity of the hair. Thus, protection of the hair shaft on the protein and fiber level is important to ensure hair has a healthy look.

Identifying the protein fragments extracted from the hair and correlating the type of protein fragment with a type of hair damage 1) enables a correct identification of the type of damage to the hair, and 2) may provide the information necessary to design products which either prevent the damage, or in the case of bleaches and/or other composition do not generate the damage. Additionally, it is also valuable to identify particular types of hair disease. Hair of individuals with hair diseases, do not react to damage and/or treatments in the same way as normal hair. Therefore, it may be possible to indicate what type of hair disease is present based upon the response of the hair at a protein level to a particular type of damage.

Also, as the protein fragment is identified, products which utilize the available bonds that result from the protein loss, in particular products specialized for specific damage types, can be produced.

SUMMARY OF THE INVENTION

The present disclosure relates generally to systems and methods for detecting types of hair damage by correlating protein fragments extracted from the hair to a type of hair damage.

A method of correlating hair damage type or source to marker protein fragments comprising: generating two identical hair samples; sample A and sample B; applying a damaging composition or treatment to sample A; apply no damaging composition or treatment to sample B; extracting the labile proteins using a suitable solvent samples from each of sample A and sample B; analyzing the protein fragment samples from sample A and sample B with MALDI-MS; comparing the MALDI-MS results from sample A and sample B; identifying the marker protein fragments by identifying the unique modification patterns which exist in sample A that do not exist in sample B.

A method for demonstrating hair damage type or source, the method comprising: extracting the labile proteins using a suitable solvent from a hair sample; analyzing the protein fragments sample with MALDI-MS; resulting in protein fragment results; and identifying the hair damage by comparing the protein fragments results to a list of marker protein fragments for particular damage.

BRIEF DESCRIPTION OF THE DRAWINGS

FIG. 1. This FIGURE is the MALDI-MS results of marker protein fragments for hair damaged by bleach in comparison to the MALDI-MS results of protein fragments for undamaged hair.

DETAILED DESCRIPTION OF THE INVENTION

As used herein, "hair" means keratinous fibers of the human or animal origin, such as hairs on the head or eyelashes. Furthermore, as used herein, the term "keratinous protein" is understood to mean those proteins present in hair. As used herein, the term "protein fragments" means the amino acids and larger proteins that are damaged and broken off the keratinous protein structure and held within the hair structure by electrostatic interactions, weak hydrogen bonding matrix proteins and lipids, or any other force that does not include incorporation in the keratinous protein structure.

As used herein "marker protein fragment" means the protein fragment which has been correlated to a particular type of hair damage and/or damaging treatment.

As used herein, "elutes," "eluting," and the like means removing proteins from hair via contacting hair with an aqueous solution without the addition of any reduction or extraction agents, thereby yielding no modification of the keratinous protein structure and no breaking or reduction of chemical bonds present in the hair sample other than electrostatic interactions, weak hydrogen bonding matrix proteins and lipids, or any other force that does not include incorporation in the keratinous protein structure.

As used herein, "elutable" means protein fragments present in the hair sample that may be removed from the hair structure in an aqueous solution without the addition of any reduction or extraction agents. Furthermore, "elutable" means proteins that may be carried out of the hair structure in an aqueous solution consisting essentially of water without the breaking or reduction of chemical bonds present in the keratinous protein structure other than electrostatic interactions, weak hydrogen bonding matrix proteins and lipids, or any other force that does not include incorporation in the keratinous protein structure.

A method has been developed for detecting and demonstrating hair damage by utilizing an aqueous solution to extract protein fragments from the hair without modifying the keratinous protein structure. One such method is described in Patent Application No. is 61/345,321 filed on May 17, 2010. Once the protein fragments are extracted from the hair, the protein fragments are analyzed. From the analysis of the protein fragments it is possible to identify the type of damage that has been done to the hair, in particular it is possible to determine the source of the damage to the hair. One such specific marker protein fragment includes those marker protein fragments generated when the hair is bleached. A hair sample can be tested, the protein fragments extracted, and the resulting protein fragments tested using an antibody based detection, and/or a mass spectrometry technique. In one embodiment the protein fragments are evaluated using the Matrix Assisted Laser Desorption Ionization ("MALDI"), also known as the MALDI-TOF Mass Spectrometry "MALDI-MS". This technique is a soft ionization technique used in mass spectrometry. MALDI-MS can be used for the analysis of biomolecules such as peptides and proteins and large organic molecules such as polymers. In MALDI, the analyte is first co-crystallized with a UV absorbing matrix such as alpha-cyano-4-hydroxycinnamic acid (CHCA), then subjected to pulse laser (YAG or nitrogen laser) radiation. This causes the vaporization/desorption of the analyte/matrix crystals and produces ions which are transmitted into a mass analyzer for detection. In MALDI-TOF, a time-of-flight mass analyzer is used. MALDI-TOF Data can be acquired in MS mode to generate molecular weight information (e.g., a peptide) and in MS/MS mode (e.g., a peptide sequence/structure information). Typical MALDI mass spectrum acquisition takes less than a minute so it can be used for fast screening of molecular species in samples of interest. Changes and molecular makers can be detected by comparing the mass spectra acquired in samples treated under different conditions such as virgin hair vs. bleached hair.

MALDI-MS can be performed either with or without enzymatic digestion of proteins. The protein fragment test results are then compared to a library of known marker protein fragments to identify what type of hair damage, and in some situations, what is the original source of damage to the hair i.e. bleach. This enables a "fingerprinting" of damage; meaning that if a hair sample is tested and the results include certain marker protein fragments, then the hair sample has been damaged by a particular source.

Additional methods for evaluating the protein fragments include, but are not limited to, liquid chromatography-electrospray mass spectrometry, antibodies against the protein fragments could be generated and an ELISA assay could be developed.

Further an iTRAQ method, reagents available through Applied Biosystems, Carlsbad Calif. can be used to establish covalent amine linkage of an isobaric tag to each lysine side chain and free N-terminal group of a protein fragment. This allows for multiple samples to be run simultaneously through the MALDI MS. Running multiple samples through the MALDI MS simultaneously minimizes variations in the test data due to test variability.

A library of these marker protein fragments can be generated by damaging swatches of hair with a variety of different compositions or treatments and then analyzing the resulting protein fragments in comparison with a similar swatch of hair which has not been damaged. Marker protein fragments can be identified by the MALDI-MS, as it is believed the same marker protein results will be found based upon the type of damage that the hair has experienced. This means that the marker protein fragment is indicative of a type or source of hair damage. Hair damages by bleach results in particular marker protein fragments, hair damaged by UV results in particular marker protein fragments etc.

It is believed that hair damaged by bleach results in +28 and +71 modification to the N-terminus of the protein fragment having the structure:

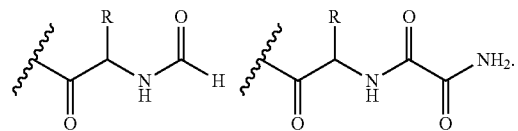

For example as indicated in FIG. 1 specific sets of fragments are released from bleached hair and extracted with water that are not present in an undamaged (virgin hair) sample. The sets of MS peaks consists of two unmodified protein peaks (966 and 1568) as well as peaks corresponding to Molecular Weights of unmodified protein peak plus 28 Daltons (966+28=994 and 1568+28=1596). The additional peaks result form chemical modification at the amine termini of the fragments. The protein fragments that correspond to the characteristic peaks are sequenced (see Table 1). Letters used to denote the protein sequences refer to the one-letter amino acid code (i.e. E=glutamic acid, I=isoleucine etc.) Additional modifications to these proteins include oxidation at Methionine, cysteine, and tryptophan residues, and deamidation at asparagine and glutamine residues can also be detected. The protein fragments mapped to Keratin 31, suggesting that this protein is degraded upon bleaching of the hair shaft.

TABLE 1

Examples of protein damage markers in bleached hair

| Marker Ion (m/z) | Protein Sequence | Modification | Protein ID |
|---|---|---|---|
| 966 | ---CNSFVR | Unmodified | Keratin 31 |
| 994 | ---CNSFVR | +28 Da @ N-terminus | Keratin 31 |
| 1037 | ---CNSFVR | +71 Da @ N-terminus | Keratin 31 |
| 1038 | ---CNSFVR | +71 Da @ N-terminus, Deamidated @ N | Keratin 31 |
| 1308 | EINTYRSLLE | +71 Da @ N-terminus | Keratin 31 |
| 1568 | EINTYRSLLESED | Unmodified | Keratin 31 |
| 1596 | EINTYRSLLESED | +28 Da @ N-terminus | Keratin 31 |
| 1639 | EINTYRSLLESED | +71 Da @ N-terminus | Keratin 31 |
| 1204 | FCEGSFNGSEK | Unmodified | Keratin 31 |
| 1205 | FCEGSFNGSEK | Asparagine (N) @ 7 deamidated | Keratin 31 |

Additionally, this method can also be used to indicate whether an individual's hair has a normal response to treatments. For example if an individual has a particular hair disease, a hair sample from this individual may not generate the same marker protein fragment as would a person who has a "normal" response. A person with a hair disease may generate additional, less and/or even different marker protein fragments than would be indicated by a normal response. A library of hair disease responses could also be created similar to that of the marker protein fragments for damage as described above. Therefore, a test for this hair disease could include exposing an individual's hair to a particular damaging treatment and then identifying the hair disease by the marker protein fragments that are generated from the damaging treatment.

In one embodiment of this hair protein loss test method the soluble and insoluble protein fragments are analyzed separately. Analyzing the soluble and insoluble protein fragments separately can result in higher sensitivity of protein fragment detection. Additionally, analyzing these protein fragments separately may further refine the determination of the location of the damage to the hair. To measure the soluble and insoluble protein fragments separately, after removal of the hair fibers the sample the in water can be centrifuged or the insoluble portion can be left to settle out from the soluble portion.

Example A

1. Bleaching of Hair to Generate Marker Protein Fragments which Indicate Damage from Bleach Hair samples were bleached using the following protocols:
Protocol #1
A bleaching solution consisting of 2% ammonium hydroxide, 0.2% tetrasodium EDTA (pH adjusted to 10.3 with acetic acid), and 6% hydrogen peroxide was prepared. Hair tresses (brown and natural white) were submerged in the bleaching solution and placed in a 40° C. oven. At timepoints of 30 to 90 minutes, hair tresses were removed from the bleaching solution, washed under DI tap water for two minutes, and dried.
Protocol #2
Identical to Protocol #1, with the exception that hydrogen peroxide (H2O2) was excluded from the bleaching solution.
Protocol #3
Identical to Protocol #1, with the exception that tetrasodium EDTA (C10H12N2O8Na4) was excluded from the bleaching solution.

2. Protein Loss Analysis of Hair Tresses Post-Bleaching

The amount of overall protein damage sustained by the hair tresses as a result of the bleaching treatments was assessed by measuring total protein loss from the hair. Briefly, 0.2-0.3 g of hair from each tress was clipped into 2 inch segments and added to a glass scintillation vial. DI water was added at a ratio of 1.0 ml DI water to 0.1 g hair, and samples were subjected to physical agitation for 60 minutes at 2,500 rpm on a vortex platform. Water extracts were analyzed for total protein concentration using the Lowry protein quantification assay. Results are summarized in Table 2.

3. MALDI-TOF Analysis of Hair Tresses Post-Bleaching

The specific protein damage sustained by the hair tresses as a result of the bleaching treatments was determined by analyzing the water extracts described above by MALDI-TOF analysis. Water extracts were mixed (1:1) directly with a MALDI matrix solution (5 mg of α-Cyano-4-hydroxycinnamic acid (CHCA) dissolved in 1 ml of 80:20:0.1 acetonitrile:water:trifluoroacetic acid). About 1 ul each sample was spotted on the MALDI plate and analyzed by MALDI-TOF/TOF 4800 plus system (AB-Sciex). Protein markers for hair damage detected in the water extracts of bleached hair include peaks with m/z 994/1037, 1596/1639, 1204, 1278 etc. Note peak 1038 is the deamidated form of 1037 and delta mass is 43 Da among the peaks 994/1037 and 1596/1639, etc. Results are summarized in Table 1 for the markers 1037 and 1204.

4. Sequencing of Protein Damage Markers from Bleached Hair

To identify and sequence of marker proteins observed in MALDI-TOF analysis, a bleached water extract were separated by a reversed phase HPLC (2 mm×15 cm, Jupiter, C4, 300A column, HP1100 system), fractions were collected manually and lyophilized. Each fraction was re-dissolved in 20 ul of 0.02% trifluoroacetic acid (TFA)/water solution, 1:1 mixed with the MALDI matrix, spotted on MALDI plate for MALDI-sequencing. For a more complete identification of proteins/proteins in the water extracts in addition those damage markers, another water extract of bleach hair was dried under vacuum and re-dissolved in 50 mM NH4Ac buffer (pH 8). 10 ul of trypsin (0.25 ug/ul in water) was added to the buffer solution and incubated at 37 C for 4 hour. The tryptic digest was dried under vacuum and re-dissolved in 50 ul of 0.02& TFA/water, followed by HPLC separation. The LC fractions were collected, dried, and analyzed by MALDI-sequencing. MALDI raw data collected from both the non-tryptic and the tryptic LC fractions was searched against protein database using ProteinPilot software (AB-Sciex). The results are summarized below.

Many different forms of hair keratins were detected in water extracts of the bleached hair after tryptic digestion. Keratins 81, 85, 31, 86, 33a, 33b, and 83 are among the major ones.

Modifications, including oxidation at Met, Cys and Trp; deamidation at Asn and Gln; formylation (+28 da to unmodified sequence) and an unknown modification (+71 da, to be further determined) at N-terminal residues were detected.

There are several pairs of proteins with delta mass 43 da, e.g., 994/1037 and 1596/1639 in the water extract and 1513/1556, 1954/1997, etc in the tryptic water extract of the bleached hair were observed. These pairs likely are the results of modifications with formylation (+28 Da) and an unknown formation (+71 Da) at N-terminal to proteins. The exact reaction chemistry of these possible modifications is unclear. These peaks and the pair (pattern) could be used as markers for hair damage.

TABLE 2

| Hair Type | Rx Time | Bleaching Protocol | Protein Concentration (μg/ml) | Marker 1037 | Marker 1204 |
|---|---|---|---|---|---|
| Natural White | 50 min | Protocol #3 | 8176.3 ug/ml | x | x |
| Natural White | 80 min | Protocol #3 | 26505.1 ug/ml | x | |
| Natural White | 90 min | Protocol #3 | 5849.3 ug/ml | x | x |
| Brown | 90 min | Protocol #3 | 230.9 μg/ml | | |
| Natural White | 30 min | Protocol #1 | 876.0 ug/ml | xxx | xxx |
| Natural White | 60 min | Protocol #1 | 1079.0 ug/ml | xxx | xxx |
| Natural White | 90 min | Protocol #1 | 2322.8 ug/ml | xx | xx |
| Brown | 90 min | Protocol #1 | 1097.8 ug/ml | x | x |
| Natural White | 90 min | Protocol #2 | 503.8 μg/ml | x | |
| Brown | 90 min | Protocol #2 | 330.0 μg/ml | | | x indicates that the marker is present

Signal intensity xxx > xx > x

Example B

Damage to hair fibers upon exposure to UV light have been documented, including impairment of mechanical properties, morphological damage, and protein loss. The specific protein breakdown caused by UV to identify peptide markers for UV damage to the hair is examined via the process defined below.

1. Ultraviolet (UV) Radiation Exposure of Hair to Generate Marker Protein Fragments which Indicate Damage from UV Protocol:

Hair tresses (General Population brown hair) were exposed to UV light for time points of up to 75 h in an Atlas Ci3000+ Xenon Arc Fade-Ometer at an irradiance setting of 1.48 W/m² at 420 nm, a chamber temperature of 35° C., and 80% relative humidity. One hour of UV exposure under the these conditions is approximately equivalent to 7.5 hours of external sun exposure in Florida, according to calculations performed using an Outdoor to Xenon Radiant Energy Conversion program provided by the manufacturer (Atlas Material Testing Technology LLC).

2. Protein Loss Analysis of Hair Tresses Post-UV: (Note: This is the Same Protocol as Used for Bleached Hair)

The amount of overall protein damage sustained by the hair tresses as a result of the UV exposure was assessed by measuring total protein loss from the hair. Briefly, 0.2-0.3 g of hair from each tress was clipped into 2 inch segments and added to a glass scintillation vial. DI water was added at a ratio of 1.0 ml DI water to 0.1 g hair, and samples were subjected to physical agitation for 60 minutes at 2,500 rpm on a vortex platform. Water extracts were analyzed for total protein concentration using the Lowry protein quantification assay. Results are summarized in Table 3.

3. MALDI-TOF Analysis of Hair Tresses Post-UV

The specific protein damage sustained by the hair tresses as a result of the UV exposure was determined by analyzing the water extracts described above by MALDI-TOF analysis. Water extracts were mixed (1:1) directly with a MALDI matrix solution (5 mg of α-Cyano-4-hydroxycinnamic acid (CHCA) dissolved in 1 ml of 80:20:0.1 acetonitrile:water: trifluoroacetic acid). About 1 ul each sample was spotted on the MALDI plate and analyzed by MALDI-TOF/TOF 4800 plus system (AB-Sciex). A protein marker for hair damage from UV was detected in the water extracts with m/z 1278. While low levels of this marker were also detected in bleached hair extracts, this marker is more abundant after UV damage and is the predominant low molecular weight fragment found after UV insult to hair. This marker was also found to increase as a function of the amount of UV exposure to the hair within a consumer-relevant exposure range (Table 3).

TABLE 3

| Hair Type | Rx Time | Approx. External Sun Exposure in Florida | m/z 1278 intensity (mean of 2x samples) |
| --- | --- | --- | --- |
| Brown | No Treatment | 0 h | 157 |
| Brown | 5 h | 38 h | 819 |
| Brown | 10 h | 75 h | 1383 |

TABLE 3-continued

| Hair Type | Rx Time | Approx. External Sun Exposure in Florida | m/z 1278 intensity (mean of 2x samples) |
| --- | --- | --- | --- |
| Brown | 20 h | 150 h | 2347 |
| Brown | 30 h | 225 h | 2597 |
| Brown | 40 h | 300 h | 4906 |
| Brown | 50 h | 375 h | 2866 |
| Brown | 75 h | 563 h | 3354 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for demonstrating bleach or UV hair damage, the method comprising:
   a) extracting the labile proteins using a suitable solvent from a hair sample to provide a protein fragment sample;
   b) analyzing the protein fragments sample with MALDI-MS; resulting in protein fragment results;
   c) identifying the hair damage by comparing the protein fragments results to a list of marker protein fragments for particular damage;
   wherein step a) comprises removing the labile protein from the hair sample via contacting the hair sample with the suitable solvent, wherein the suitable solvent is an aqueous solution without the addition of any reduction or extraction agents;
   wherein the MALDI-MS is performed without the enzymatic digestion of proteins; and
   wherein the list of marker protein fragments include a +28 and +71 modification to the N-terminus of the protein fragment having the structure:

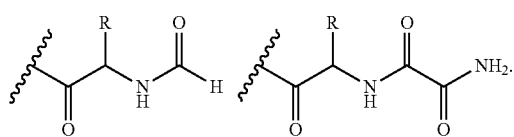

for identifying bleach damage, or a protein marker with m/z 1278 for identifying UV damage.

* * * * *